US010724355B2

(12) United States Patent
Jones et al.

(10) Patent No.: US 10,724,355 B2
(45) Date of Patent: Jul. 28, 2020

(54) DOWNHOLE TOOLS AND METHODS FOR ISOLATING AND ANALYZING GASES FROM DOWNHOLE FLUIDS

(71) Applicant: Halliburton Energy Services, Inc., Houston, TX (US)

(72) Inventors: Christopher M. Jones, Katy, TX (US); Darren Gascooke, Houston, TX (US); Anthony H. van Zuilekom, Houston, TX (US); Michael T. Pelletier, Houston, TX (US); Bin Dai, Spring, TX (US); James M. Price, The Woodlands, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 178 days.

(21) Appl. No.: 15/751,254

(22) PCT Filed: Dec. 19, 2016

(86) PCT No.: PCT/US2016/067624
§ 371 (c)(1),
(2) Date: Feb. 8, 2018

(87) PCT Pub. No.: WO2018/118017
PCT Pub. Date: Jun. 28, 2018

(65) Prior Publication Data
US 2019/0284919 A1      Sep. 19, 2019

(51) Int. Cl.
*E21B 49/08* (2006.01)
*E21B 43/38* (2006.01)
(Continued)

(52) U.S. Cl.
CPC ............ *E21B 43/38* (2013.01); *E21B 49/082* (2013.01); *G01N 1/2247* (2013.01); *G01N 1/40* (2013.01);
(Continued)

(58) Field of Classification Search
CPC .. E21B 43/38; E21B 49/082; E21B 2049/085; E21B 49/081; G01N 21/85;
(Continued)

(56) References Cited

U.S. PATENT DOCUMENTS 5,859,430 A * 1/1999 Mullins ................. E21B 47/102
250/255
8,760,644 B2   6/2014 Seckar
(Continued)

FOREIGN PATENT DOCUMENTS

WO   2014042642 A1   3/2014
WO   2014133764 A1   9/2014
WO   2016108918      7/2016

OTHER PUBLICATIONS

International Search Report and Written Opinion of PCT Application No. PCT/US2016/067624 dated Aug. 18, 2017: pp. 1-16.

*Primary Examiner* — Brad Harcourt
(74) *Attorney, Agent, or Firm* — Chamberlain Hrdlicka

(57) ABSTRACT

Downhole tools for isolating and analyzing one or more gases include a gas separation assembly in fluid communication with a gas specific analyzer. The gas separation assembly includes a piston disposed within a housing and a separation volume defined between the piston and the housing. The piston is movable to separate a gas component and a liquid component from a downhole formation fluid within the separation volume. The gas specific analyzer is operable to measure one or more properties of the gas component. In some configurations, the gas specific analyzer is an optical assembly containing a light source, an optical detector, and (Continued)

a gas cell that contains an observation volume. The optical assembly is operable to measure one or more properties of the gas component within the observation volume via the light source and the optical detector.

18 Claims, 9 Drawing Sheets

(51) Int. Cl.
  *G01N 1/22* (2006.01)
  *G01N 21/85* (2006.01)
  *G01N 33/24* (2006.01)
  *G01N 1/40* (2006.01)
(52) U.S. Cl.
  CPC ......... *G01N 21/85* (2013.01); *G01N 21/8507* (2013.01); *G01N 33/241* (2013.01); *G01N 2001/2267* (2013.01); *G01N 2021/855* (2013.01)

(58) Field of Classification Search
  CPC .... G01N 1/40; G01N 33/241; G01N 21/8507; G01N 1/2247; G01N 2021/855; G01N 2001/2267
  See application file for complete search history.

(56) References Cited

U.S. PATENT DOCUMENTS

| | | |
|---|---|---|
| 9,435,729 B2 | 9/2016 | Bernhard |
| 2007/0030482 A1 | 2/2007 | Ji et al. |
| 2013/0156646 A1 | 6/2013 | Bernhard |
| 2014/0238667 A1 | 8/2014 | Dumont et al. |
| 2014/0361155 A1 | 12/2014 | Daito et al. |
| 2015/0247950 A1 | 9/2015 | Perkins |
| 2016/0032718 A1 | 2/2016 | Jones et al. |
| 2016/0084068 A1 | 3/2016 | Pelletier et al. |
| 2016/0139085 A1 | 5/2016 | Pelletier et al. |
| 2016/0178837 A1 | 6/2016 | Pelletier et al. |

\* cited by examiner

DOWNHOLE TOOLS AND METHODS FOR ISOLATING AND ANALYZING GASES FROM DOWNHOLE FLUIDS

BACKGROUND

This section is intended to provide relevant background information to facilitate a better understanding of the various aspects of the described embodiments. Accordingly, it should be understood that these statements are to be read in this light and not as admissions of prior art.

Devices have been used in downhole environments to measure various properties of liquid phase components of drilling fluids, formation fluids, and other downhole fluids found in wellbores formed in subterranean formations. The determination of any gas phase components for these types of downhole fluids can provide valuable and useful information. However, the gas phase components found in such downhole fluids are typically difficult to measure in the presence of the liquid phase components. Devices for measuring gases are susceptible to interferences and scattering, reactive components, and equilibrium difficulties with multiphase behavior of the downhole fluids.

BRIEF DESCRIPTION OF THE DRAWINGS

Embodiments of the invention are described with reference to the following figures. The same numbers are used throughout the figures to reference like features and components. The features depicted in the figures are not necessarily shown to scale. Certain features of the embodiments may be shown exaggerated in scale or in somewhat schematic form, and some details of elements may not be shown in the interest of clarity and conciseness.

DETAILED DESCRIPTION

Figure 1:
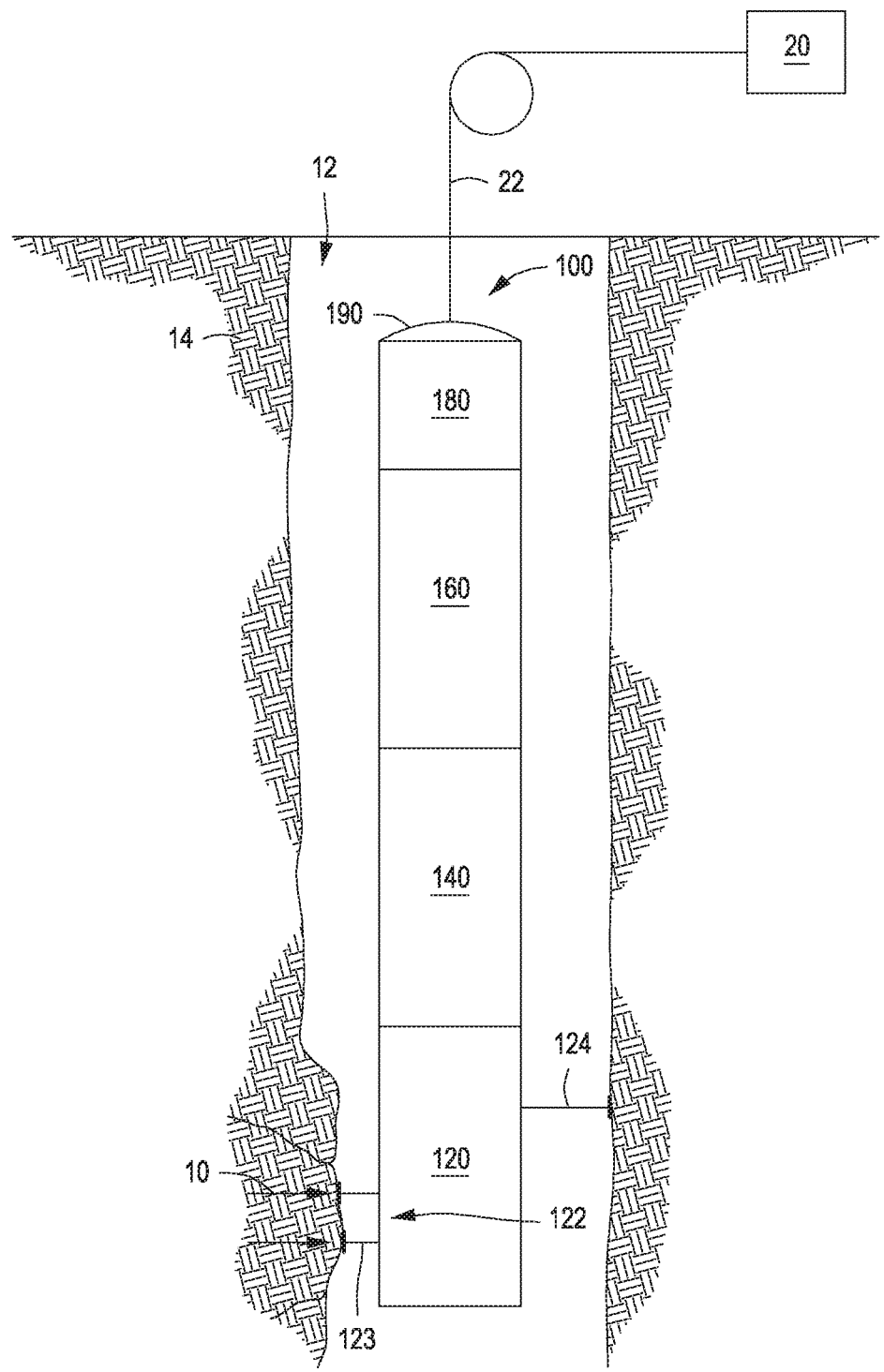
FIG. 1 depicts a schematic view of downhole tool for isolating and analyzing a gas, according to one or more embodiments.

FIG. 1 depicts a schematic view of a downhole tool 100, according to one or more embodiments. The downhole tool 100 is a formation testing tool and can be used to isolate and analyze one or more gases (e.g., mercury, hydrogen sulfide, a mercaptan) from a downhole formation fluid, depicted by arrows 10, within a wellbore 12 extending into a subterranean formation 14. The downhole tool 100 is suspended or otherwise located within the wellbore 12 by a wireline cable 22 that connects the downhole tool 100 to a surface control unit 20. Alternatively, the downhole tool 100 can be deployed in the wellbore 12 on coiled tubing, jointed drill pipe, hard wired drill pipe, or any other suitable deployment technique (not shown).

The downhole tool 100 includes a fluid acquisition section 120, a gas-liquid separation section 140, an gas analysis section 160 (e.g., optical section), a pump section 180, and a downhole control system section 190. One, two, or more extendable tool anchors 124 are positioned on any one or more portions or sections of the downhole tool 100. For example, one or more extendable tool anchors 124 are on the fluid acquisition section 120, the gas-liquid separation section 140, the gas analysis section 160, the pump section 180, the downhole control system section 190, or other sections.

The fluid acquisition section 120 includes a fluid probe assembly 122 containing one, two, or more extendable fluid admitting probes 123 (two are shown in FIG. 1). The fluid probe assembly 122 and the probes 123 draw or uptake the downhole formation fluid 10 from select portions of the formation 14 while avoiding other portions of the formation 14 that can contain mud, frac or drilling fluid, and/or other contaminants. The downhole formation fluid 10 is drawn, flowed, introduced, or otherwise transferred into the fluid acquisition section 120 through the probe assembly 122 by a suction generated by in the pump section 180.

The downhole formation fluid 10 is flowed from the fluid acquisition section 120 to the gas-liquid separation assembly 140 where the downhole formation fluid 10 is separated into one or more gas components and one or more liquid components. The gas component can be or include, but is not limited to, mercury, hydrogen sulfide, one or more mercaptans, one or more other sulfur-containing compounds, or any mixture thereof. The liquid component can be or include, but is not limited to, crude oil, downhole water, drilling fluid, frac fluid, drilling fluid filtrate, or any mixture thereof.

The one or more gas components are flowed from the gas-liquid separation assembly 140 to the gas analysis section 160 and analyzed therein. Data generated or otherwise produced the gas analysis section 160 is transferred from the gas analysis section 160 and/or the downhole control system section 190 to the surface control unit 20 by the wireline cable 22.

Figure 2:
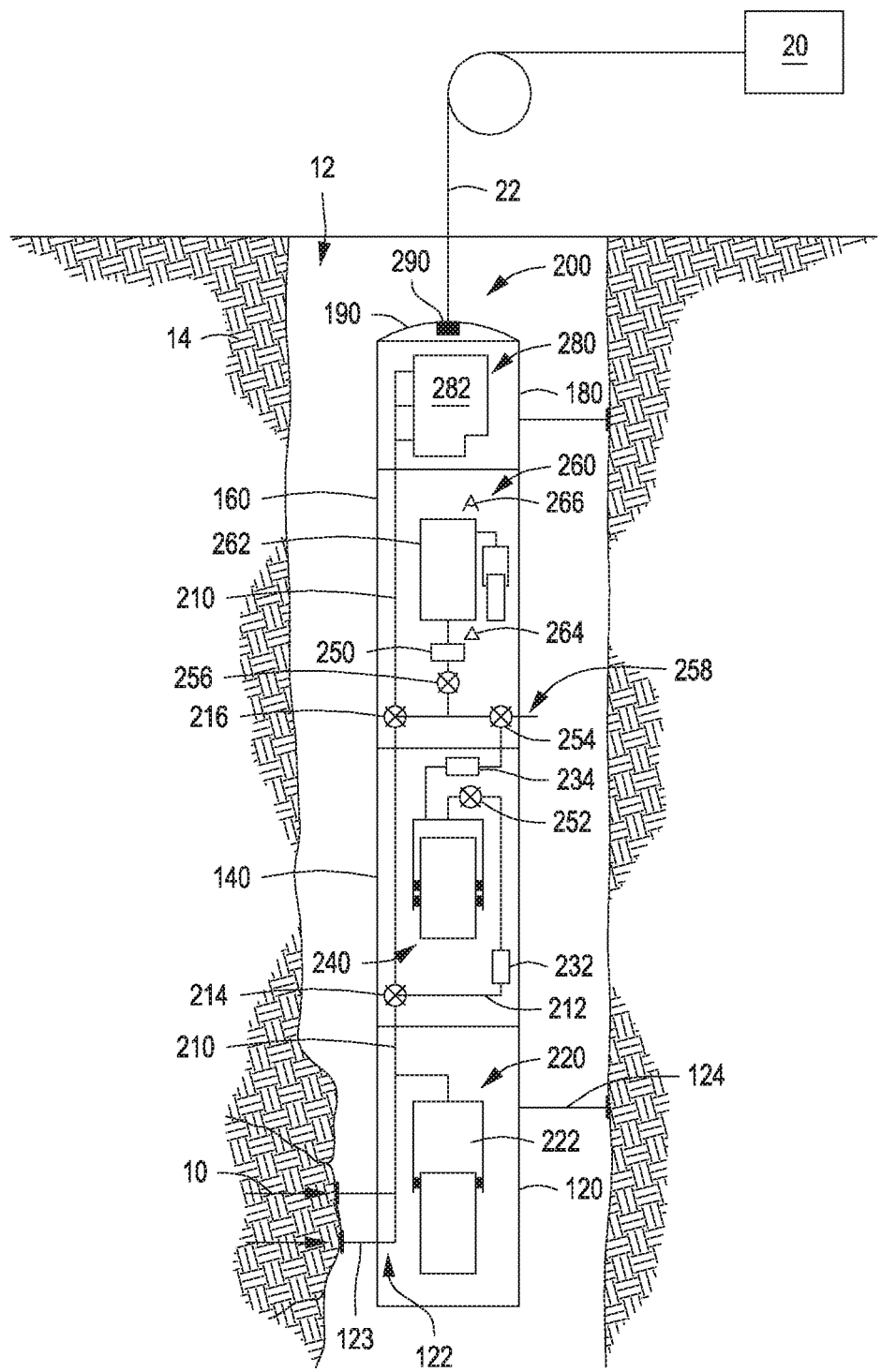
FIG. 2 depicts a schematic view of another downhole tool for isolating and analyzing a gas, according to one or more embodiments.

FIG. 2 depicts a schematic view of a downhole tool 200, according to one or more embodiments. In one or more embodiments, the downhole tool 200 is positioned in the wellbore 12, connected to the surface control unit 20 and the wireline cable 22, and includes the fluid acquisition section 120, the gas-liquid separation section 140, the gas analysis section 160, the pump section 180, and the downhole control system section 190, as described for the downhole tool 100.

The downhole tool 200 or portions thereof depicted in FIG. 2 and the downhole tool 100 or portions thereof depicted FIG. 1 share many common components. It should be noted that like numerals shown in the Figures and discussed herein represent like components throughout the multiple embodiments disclosed herein.

The downhole tool 200 isolates and analyzes one or more gases from the downhole formation fluid 10 from the subterranean formation 14 within the wellbore 12. In one or more embodiments, the downhole tool 200 includes a fluid acquisition assembly 220 in the fluid acquisition section 120, a gas separation assembly 240 in the gas-liquid separation section 140, a gas specific analyzer 260 in the gas analysis section 160, a pump assembly 280 in the pump section 180, and a control system 290 in the downhole control system section 190.

The downhole tool 200 and portions thereof can include one or more protective materials to minimize or prohibit undesired interactions with one or more gas components and/or one or more liquid components within the downhole formation fluid, as well as other gases or liquids that may be downhole in the wellbore 12. The downhole tool 200, assemblies thereof, and portions thereof can include, but are not limited to, one or more inner surfaces and/or one or more outer surfaces of the fluid acquisition section 120 including the fluid acquisition assembly 220, the gas-liquid separation section 140 including the gas separation assembly 240, the gas analysis section 160 including the gas specific analyzer 260, the pump section 180 including the pump assembly 280, the downhole control system section 190 including the control system 290, or components thereof. These components, assemblies, and/or surfaces can be made of or from one or more protective materials and/or can have a coating or plating containing one or more protective materials. The protective material can minimize or prohibit undesired interactions, such as chemical reactions and adsorption. Exemplary protective materials can be or include, but are not limited to, one or more nickel alloys, one or more nickel-chromium-iron alloys, one or more silicon coatings, one or more amorphous silicon coatings, one or more aluminum oxide coatings, one or more sapphire coatings, one or more steels, one or more stainless steels, alloys thereof, or any mixture thereof.

Nickel alloys, such as the HASTELLOY® alloys, are commercially available from Haynes International, Inc., and can include nickel and any of the following elements: molybdenum, chromium, cobalt, iron, copper, manganese, titanium, zirconium, aluminum, carbon, and/or tungsten. Nickel-chromium-iron alloys, such as inconel alloys, can include nickel, chromium, iron, and any of the following elements: molybdenum, niobium, cobalt, copper, manganese, titanium, aluminum, silicon, carbon, sulfur, phosphorous, and/or boron. Amorphous silicon coatings, such as SILCONERT®, SILTEK®, and/or SUILFINERT® coatings, are commercially available from the SilcoTek Corporation.

One or more primary fluid lines 210 are coupled to and in fluid communication with the fluid acquisition assembly 220 and the pump assembly 280. One or more bypass fluid lines 212 are coupled to and in fluid communication with the primary fluid line 210, such as at one, two, or more junctions along the primary fluid line 210 between the fluid acquisition assembly 220 and the pump assembly 280. The primary fluid line 210 and the bypass fluid line 212 are isolatable from one another by one, two, or more valves 214, 216 used to control the fluid communication therebetween. In some examples, the valves 214, 216 can include, but are not limited to, two stop valves, two three-way valves, or one stop valve and one three-way valve. In other examples, the valves 214, 216 can include a one-way check valve and either a stop valve or a three-way valve.

The downhole formation fluid flows or passes from the fluid acquisition section 120, through the gas-liquid separation section 140 and the gas analysis section 160, and into the pump section 180 via the primary fluid line 210. The valves 214, 216 are operated to isolate the bypass fluid line 212 from the primary fluid line 210 such that a portion of the downhole formation fluid is contained in and flowed through the bypass fluid line 212 and directed into the gas-liquid separation section 140. Once separated from the downhole formation fluid, the gas component can be transferred to the gas separation assembly 240 in the gas-liquid separation section 140 via the bypass fluid line 212. Also, the liquid component can be transferred out of the downhole tool 200 via the bypass fluid line 212, as further discussed below. In one or more configurations, the bypass fluid line 212 is used to flow the downhole formation fluid, one or more gas components, one or more liquid components, or any mixture thereof.

The bypass fluid line 212 can also include an exit line 258 having an exit port extending outside of the downhole tool 200 and into the wellbore 12. The exit line 258 is isolatable from the bypass fluid line 212 by one or more valves 254 (one valve is shown in FIG. 2). The exit line 258 can eject or otherwise flow one or more fluids, such as, but not limited to, the downhole formation fluid, one or more gas components, one or more liquid components, or any mixture thereof, into the wellbore 12 from the bypass fluid line 212.

The fluid acquisition assembly 220 receives in the downhole formation fluid. To do so, the one or more probes 123 of the fluid probe assembly 122 extend away from the fluid acquisition assembly 220 (e.g., outside of downhole tool 200) and into the wellbore 12 toward the formation 14. The fluid probe assembly 122 is in fluid communication with the primary fluid line 210 and thus may uptake, admit, or transfer the downhole formation fluid from the formation 14 within the wellbore 12 into the fluid acquisition assembly 220.

One or more pumps 282 within the pump assembly 280 are coupled to the primary fluid line 210 downstream of the bypass fluid line 212. Illustrative pumps 282 can be or include, but are not limited to, hydraulic pumps, flushing pumps, rotary pumps, other types of pumps, or combinations thereof. The pump 282 generates a suction to draw, flow, or otherwise transfer the downhole formation fluid 10 through the probe assembly 122 and into the primary fluid line 210, the bypass fluid line 212, and throughout the assemblies 220, 240, 260, and 280 of the downhole tool 200.

The downhole tool 200 also includes one or more pre-test units 222 located in the fluid acquisition assembly 220 and coupled to the primary fluid line 210. For example, the pre-test unit 222 can be coupled to the primary fluid line 210 downstream of the fluid probe assembly 122 and upstream of the bypass fluid line 212. The pre-test unit 222 can be or include, but is not limited to, one or more canisters, vials, ampoules, or other type of containers. An aliquot or sample of the downhole formation fluid is transferred from the formation 14 to the pre-test unit 222 and stored for later testing and analysis.

The gas separation assembly 240 is coupled to and in fluid communication with the bypass fluid line 212 and/or contained within the gas-liquid separation section 140. In other configurations, as further discussed below, the gas separation assembly 240 is optionally substituted with a gas separation assembly 300 (FIG. 3), a gas separation assembly 400 (FIG. 4), or other gas separation assemblies that is coupled to and in fluid communication with the bypass fluid line 212 and/or contained within the gas-liquid separation section 140.

One, two, or more fluid sensors 232, 234 are on the bypass fluid line 212 and used to measure the density of the downhole formation fluid at that portion of the bypass fluid line 212. For example, a first fluid sensor 232 is located on the bypass fluid line 212 upstream of the gas separation assembly 240 and used to measure the density of the downhole formation fluid before entering the gas separation assembly 240. Also, a second fluid sensor 234 is located on the bypass fluid line 212 downstream of the gas separation assembly 240 and used to measure the density of the downhole formation fluid after exiting the gas separation assembly 240. In one or more embodiments, each of the fluid sensors 232, 234 can independently be or include, but is not limited to a density sensor, a temperature sensor, a pressure sensor, a combined temperature-pressure sensor, a viscosity sensor, a composition sensor, or any combination thereof.

The gas specific analyzer 260 is coupled to and in fluid communication with the bypass fluid line 212 and/or contained within the gas analysis section 160. In one or more embodiments, the gas specific analyzer 260 is an optical assembly that can include, but is not limited to, one or more gas cells 262, one or more light sources 264, and/or one or more optical detectors 266. The gas specific analyzer 260 receives one or more gas components from the gas separation assembly 240 and measures one or more properties of each gas component. For example, when the gas specific analyzer 260 is or includes an optical assembly, the gas component is within the gas cell 262 and the properties of the gas component are measured via the light source 264 and the optical detector 266. In other configurations, as further discussed below, the gas specific analyzer 260 can be substituted with one or more optical assemblies 500, 600, 700, 800, or 900, as depicted in FIG. 5-9, or other optical assemblies that are coupled to and in fluid communication with the bypass fluid line 212 and/or contained within the gas analysis section 160.

One or more liquid rejection devices 250 and/or one or more valves 256 can be disposed within the gas analysis section 160. For example, the liquid rejection device 250 and/or the valve 256 can be located on or coupled to the bypass fluid line 212 between the gas separation assembly 240 and the gas specific analyzer 260. The liquid rejection device 250 and/or the valve 256 reduce and/or prevent water or other liquids from flowing into the gas specific analyzer 260, such as from the bypass fluid line 212 and/or the gas separation assembly 240. The liquid rejection device 250 can be or include, but is not limited to, one or more gas permeable membranes, a liquid or solvent trap, a centrifuge, or any combination thereof.

Figure 10:
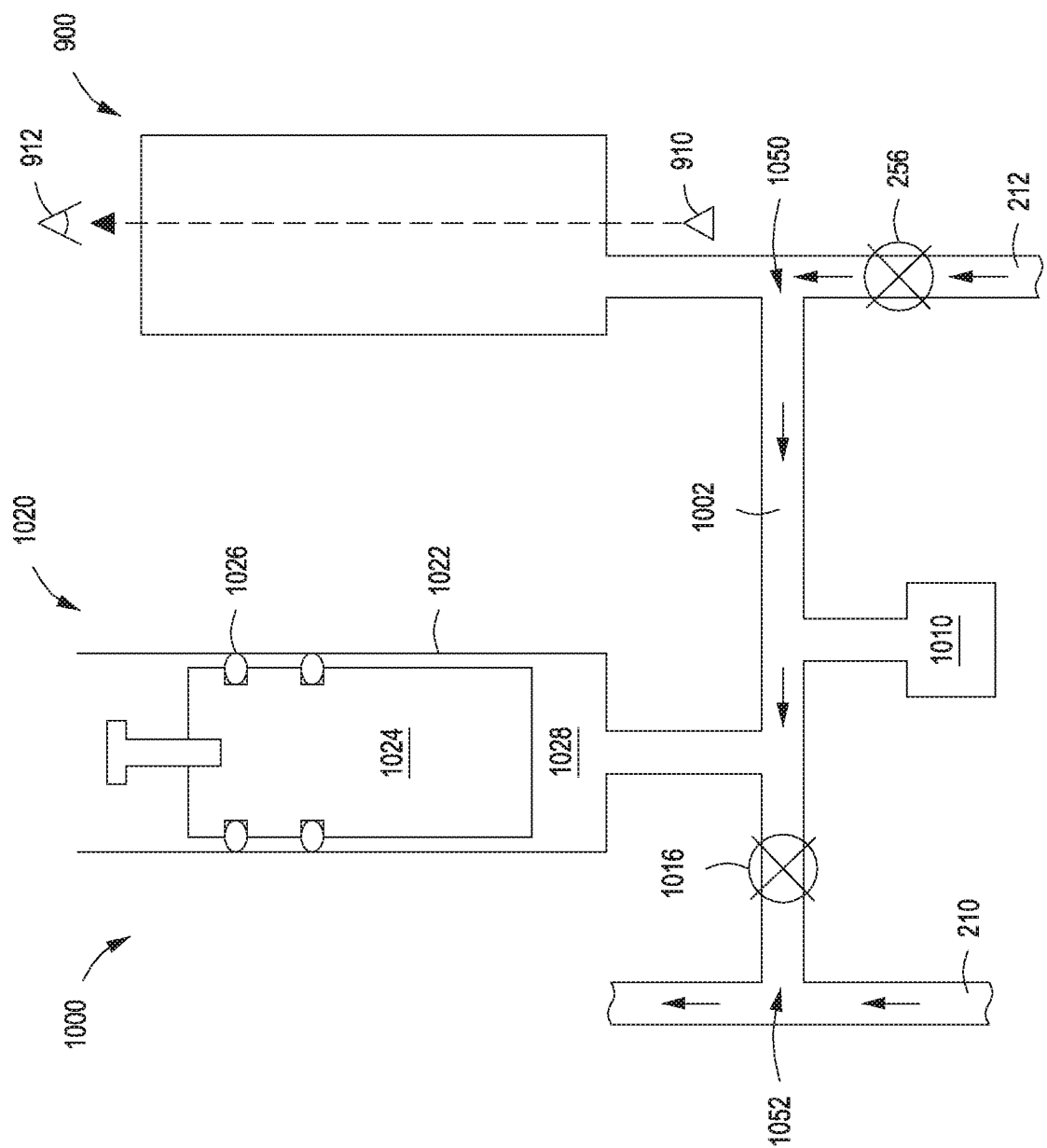
FIG. 10 depicts a schematic view of a liquid rejection device and another optical assembly that are optionally used in a downhole tool for isolating and analyzing a gas, according to one or more embodiments.

In one or more examples, not shown in FIG. 2, the liquid rejection device 250 can be or include one or more liquid traps, one or more trap lines, one or more pistons, one or more purge lines. In one configuration, the trap line is coupled to and between the liquid trap and the bypass fluid line, and the purge line is coupled to and between the liquid trap and the primary fluid line 210. An exemplary liquid rejection device containing a liquid trap is further described and disclosed below as well as depicted in FIG. 10.

Although not shown in FIG. 2, the downhole tool 200 can also include one or more sensors. The sensor can be or include, but is not limited to, a temperature sensor, a pressure sensor, a combined temperature-pressure sensor, a density sensor, a viscosity sensor, a composition sensor, or any combination thereof disposed within the gas specific analyzer 260, the bypass fluid line 212, or both of the gas specific analyzer 260 and the bypass fluid line 212. These sensors are further described and discussed below and shown in the specified Figures.

Figure 3:
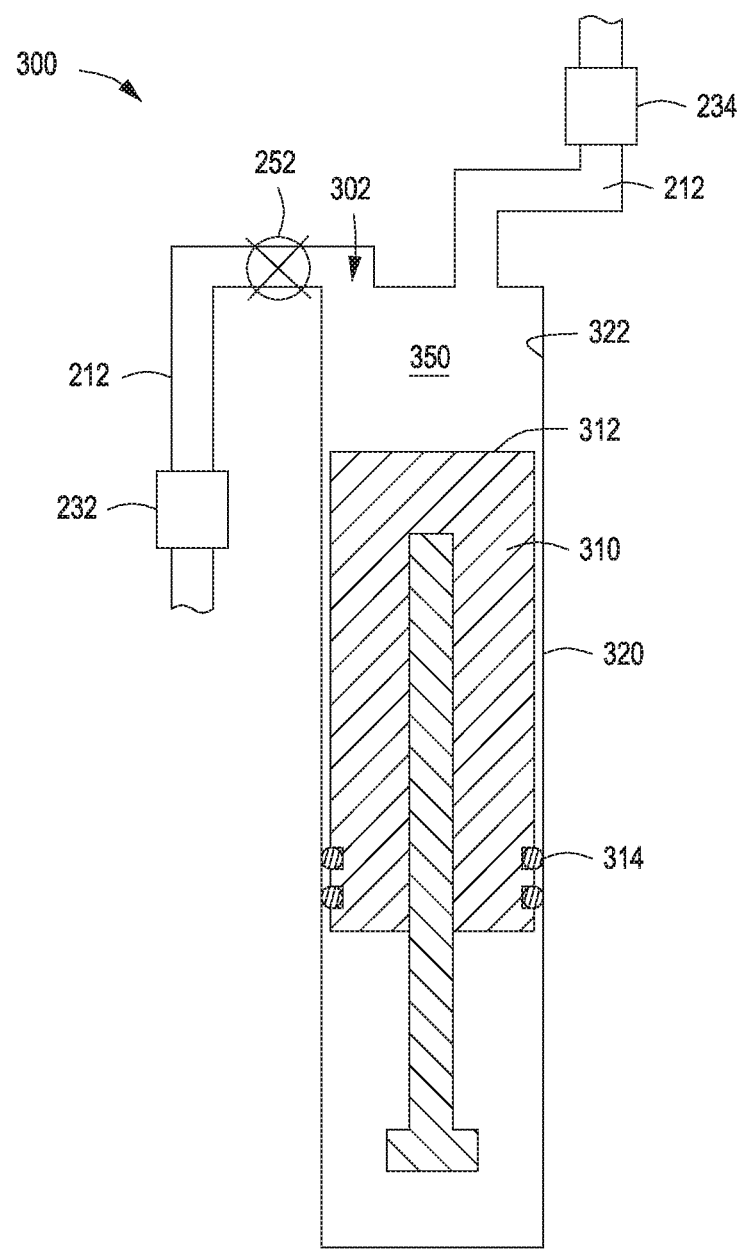
FIG. 3 depicts a schematic view of a gas separation assembly that is optionally used in a downhole tool for isolating and analyzing a gas, according to one or more embodiments.

FIG. 3 depicts a schematic view of a gas separation assembly 300 that can be in the gas-liquid separation section 140 and can be used in the downhole tool 100, 200 to isolate one or more gas components, according to one or more embodiments. The gas separation assembly 300 includes a piston 310 contained at least partially within a body or housing 320. The inner end or the upper surface 312 of the piston 310 and the inner surface 322 of the housing 320 provide a volume or a space therebetween that is referred to as a separation volume 350. The separation volume 350 is defined as the volume located between the upper surface 312 of the piston 310 and the inner surface 322 of the housing 320, as depicted in FIG. 3. One or more sealing elements or sealants 314 are positioned between the piston 310 and the housing 320 to produce a seal (e.g., gas and/or liquid seal) therebetween. The sealing element or sealant 314 can be or include, but is not limited to, one or more O-rings, one or more gaskets, grease, or any combination thereof.

One or more fluid ports 302 can be disposed in an upper portion of the housing 320. The fluid port 302 introduces the downhole formation fluid into the separation volume 350 above the upper surface 312 of the piston 310. The gas separation assembly 300 receives the downhole formation fluid from the bypass fluid line 212.

The piston 310 is moveable relative to the housing 320. For example, the piston 310 is axially moveable relative to the housing 320 so to move away from the fluid port 302 to increase the volume of the separation volume 350 and toward the fluid port 302 to decrease the volume of the separation volume 350. The piston 310 can be moved by, but not limited to, a hydraulic motor, a pneumatic motor, an electric motor, or any combination thereof.

The gas separation assembly 300 separates one or more gas components and one or more liquid components from the downhole formation fluid within the separation volume 350. For example, the separation volume 350 is increased by moving the piston 310 away from the fluid port 302. The increased volume of the separation volume 350 decreases the pressure therein to provide separation of at least a portion of the gas components from the downhole formation fluid while leaving behind at least a portion of the liquid components. The piston can be adiabatically moved to decrease the pressure sufficiently to separate the gas component from the downhole formation fluid and leave behind the liquid component.

Figure 4:
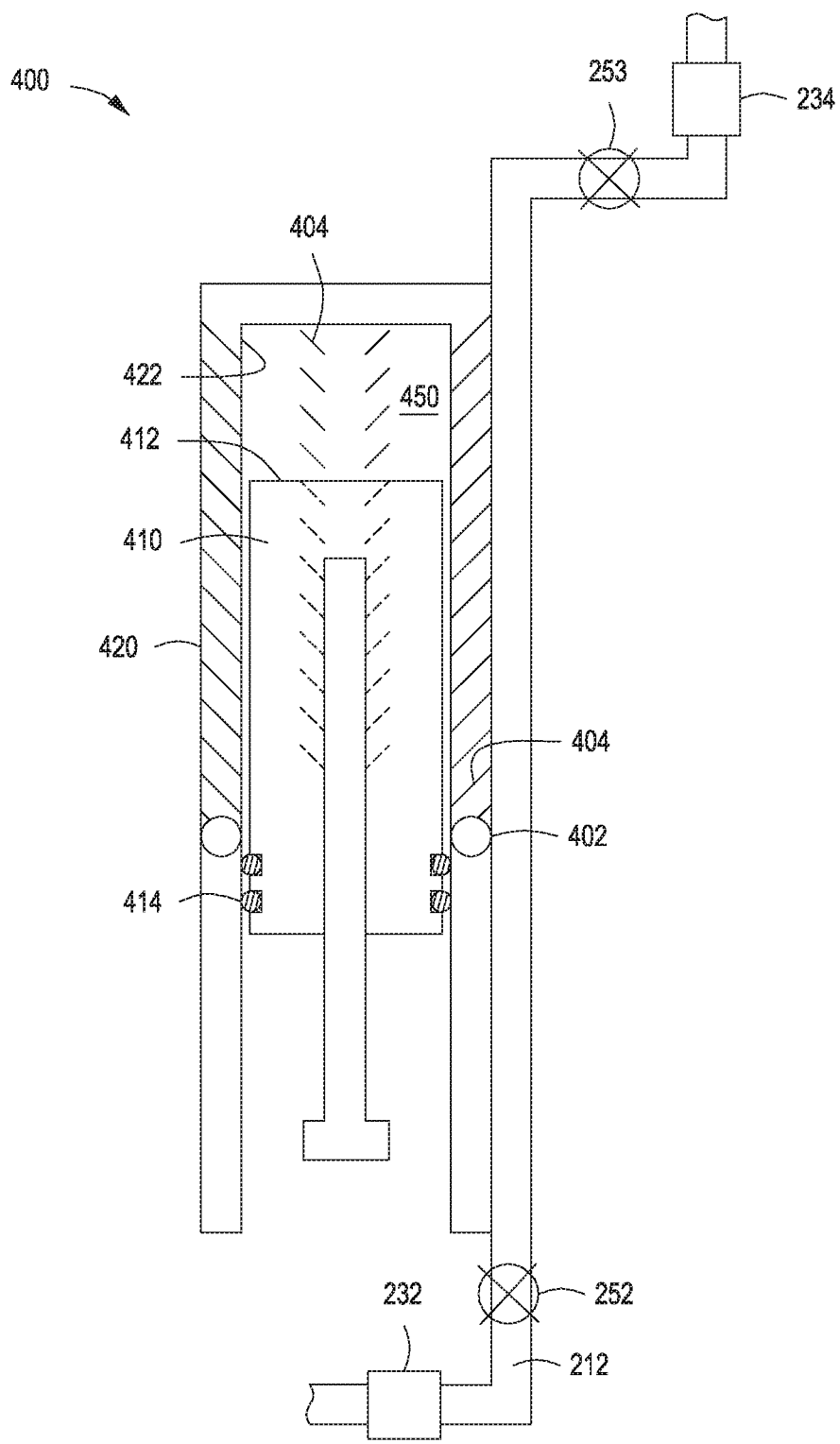
FIG. 4 depicts a schematic view of another gas separation assembly that is optionally used in a downhole tool for isolating and analyzing a gas, according to one or more embodiments.

FIG. 4 depicts a schematic view of a gas separation assembly 400 that can be located in the gas-liquid separation section 140 and used in the downhole tool 100, 200 to isolate one or more gas components, according to one or more embodiments. The gas separation assembly 400 includes a piston 410 contained at least partially within a body or housing 420, one or more fluid passageways 402 formed in or located on the housing 420, and one or more fluid slits 404 formed through at least a portion of the housing 420.

The inner end or an upper surface 412 of the piston 410 and the inner surface 422 of the housing 420 provide a volume or a space therebetween that is referred to as a separation volume 450. The separation volume 450 is defined as the volume located between the upper surface 412 of the piston 410 and the inner surface 422 of the housing 420, as depicted in FIG. 4. One or more sealing elements or sealants 414 are positioned between the piston 410 and the housing 420 to produce a seal (e.g., gas and/or liquid seal) therebetween. The sealing element or sealant 414 can be or include, but is not limited to, one or more O-rings, one or more gaskets, grease, or any combination thereof.

The gas separation assembly 400 receives the downhole formation fluid from the bypass fluid line 212. More specifically, the downhole formation fluid can pass, flow, or otherwise be transferred from the bypass fluid line 212, through the fluid passageway 402, and to the fluid slits 404.

The one or more fluid passageways 402 can be or include, but are not limited to, one or more grooves, one or more lips, one or more conduits (e.g., piping or tubing), or any combination thereof. The one or more fluid passageways 402 are positioned at least partially around the circumference of an inner surface of the housing 420.

The one or more fluid slits 404 are located along one or more vertical sides of the housing 420. One, two, three, four, five, or more arrays of fluid slits 404 can be vertically arranged (four arrays are shown in FIG. 4) along the inner surface of the housing 420. The arrays of the fluid slits 404 are positioned to introduce the downhole formation fluid into the separation volume 450 above the upper surface 412 of the piston 410. In one or more configurations, the gas separation assembly 400 also includes a first plurality of fluid slits 404 located along a first vertical side of the body and a second plurality of fluid slits 404 located along a second vertical side of the body. The fluid slits 404 are positioned to introduce the downhole formation fluid into the separation volume along the vertical sides of the housing 420 and above an upper surface of the piston 410. The first and second pluralities of the fluid slits 404 are in fluid communication with the fluid passageway 402.

The piston 410 is moveable relative to the housing 420. For example, the piston 410 is axially moveable relative to the housing 420 so to move away from the fluid port 402 to increase the volume of the separation volume 450 and toward the fluid port 402 to decrease the volume of the separation volume 450. The piston 410 can be moved by, but not limited to, a hydraulic motor, a pneumatic motor, an electric motor, or any combination thereof.

The movement of the piston 410 relative to the housing 420 can provide control of the rate of admission or introduction of the downhole formation fluid into the separation volume 450 due to the change in volume and pressure relative to the movement of the piston 410. Also, the gas separation assembly 400 separates one or more gas components and one or more liquid components from the downhole formation fluid within the separation volume 450. For example, the separation volume 450 is increased by moving the piston 410 away from the fluid port 402. The increased volume of the separation volume 450 decreases the pressure therein to provide separation of at least a portion of the gas components from the downhole formation fluid while leaving behind at least a portion of the liquid components.

FIGS. 5-9 depict schematic views of optical assemblies 500, 600, 700, 800, and 900, respectively, according to one or more embodiments. The optical assembly 500, 600, 700, 800, or 900 can be within the gas analysis section 160 and used in the downhole tool 100, 200 to analyze one or more gas components, according to one or more embodiments. The optical assembly 500, 600, 700, 800, or 900 can be coupled to and in fluid communication with the bypass fluid line 212. The optical assembly 500, 600, 700, 800, or 900 can be isolated from a remainder of the bypass fluid line 212 via one or more valves 256, such as a stop valve.

Each of the optical assemblies 500, 600, 700, 800, and 900 includes one or more light sources 510, 610, 710, 810, and 910 and one or more optical detectors 512, 612, 712, 812, and 912, respectively. The light sources 510, 610, 710, 810, and 910 can emit light (e.g., optical beam) in at least the ultraviolet (UV) spectrum, but may also emit in the visible spectrum and/or the infrared (IR) spectrum. The light sources 510, 610, 710, 810, and 910 can be or include, but are not limited to, one or more deuterium lamps, one or more mercury lamps, one or more broadband light sources, or a combination thereof. The optical detectors 512, 612, 712, 812, and 912 can absorb or otherwise detect in at least the UV spectrum, but may also detect in the visible spectrum and/or the IR spectrum. The optical detectors 512, 612, 712, 812, and 912 can be or include, but are not limited to, one or more photomultiplier tubes, one or more silicon photodiodes, one or more integrated computational element (ICE) cores, one or more filters, one or more lenses, one or more mirrors, filter photometer, dispersive element such as a grating (monochromator) spectrometer, or any combination thereof. In some examples, an optical range for detecting hydrogen sulfide is about 150 nm to about 250 nm, about 150 nm to about 200 nm, or about 175 nm to about 225 nm. In some configurations, an ICE core or a combination of multiple ICE cores is used as a non-dispersive analytical element One or more liquid rejection devices 250 and/or the valve 256 is located on or within the gas analysis section 160 and/or positioned on or coupled to the bypass fluid line 212 between the gas separation assembly 240 and the optical assembly 500, 600, 700, 800, or 900. The liquid rejection device 250 and/or the valve 256 reduce and/or prevent water or other liquids from flowing into the optical assembly 500, 600, 700, 800, or 900, such as from the bypass fluid line 212 and/or the gas separation assembly 240.

Figure 5:
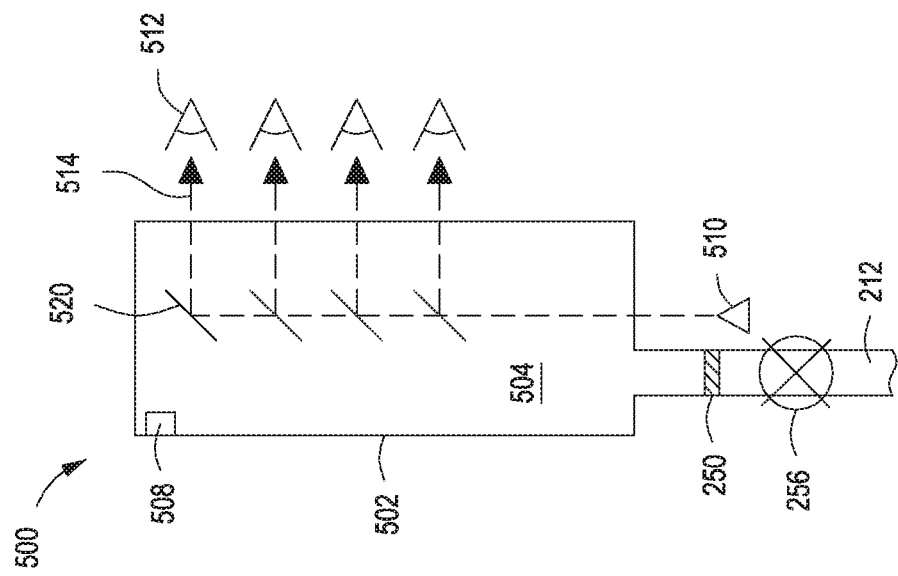
FIG. 5 depicts a schematic view of an optical assembly that is optionally used in a downhole tool for isolating and analyzing a gas, according to one or more embodiments.

The optical assembly 500 depicted in FIG. 5 can include one or more gas cells 502, one or more light sources 510, one or more optical detectors 512, and one or more reflective surfaces 520. For example, as depicted in FIG. 5, the optical assembly 500 has one light source 510, four optical detectors 512, and four reflective surfaces 520. In other configurations, the optical assembly 500 includes 1, 2, 3, 4, 5, 6, or more for each of the light sources 510, the optical detectors 512, and the reflective surfaces 520.

The light source 510 and the optical detector 512 are outside of the gas cell 502 and the reflective surface 520 is positioned inside the gas cell 502, as depicted in FIG. 5. In other configurations, not shown, any of the light source 510, the optical detector 512, and the reflective surface 520 can independently be inside or outside of the gas cell 502. The optical detector 512 can be located on an adjacent side of the gas cell 502 relative to the light source 510, as depicted in FIG. 5. In other examples, not shown, the optical detector 512 can be located on the same side and/or the opposite side of the gas cell 502 relative to the light source 510.

The reflective surface 520 can be or include one or more mirrors and/or one or more arrays of mirrors. The reflective surface 520 can be or include one or more semi-transparent mirrors and/or one or more non-transparent mirrors. In one or more embodiments, the semi-transparent mirrors contain or are made from one or more semi-transparent materials. Illustrative semi-transparent materials, are not limited by, but can absorb, scatter, and/or lose, for example, about 25% to about 50% of light shined thereto.

The optical assembly 500 has an observation volume 504 defined by the available volume or space, fixed or variable, within the gas cell 502. The optical assembly 500 receives the gas component from the gas separation assembly 240 and measure a property of the gas component within the observation volume 504 of the gas cell 502 via the light source 510 and the optical detector 512.

Optical beams emitted by the light source 510 follow one, two, three, four, or more light paths 514 that extend between any of the light sources 510, the reflective surfaces 520, and the optical detectors 512. For example, the light paths 514 extend from the light source 510 to any of the reflective surfaces 520 and from the reflective surface 520 to any of the optical detectors 512. An array of reflective surfaces 520 at different distances from the light source 510 provide light paths 514 having proportionally different lengths.

The optical assembly 500 can also include one or more sensors 508. The sensor 508 can be or include, but is not limited to, a temperature sensor, a pressure sensor, a combined temperature-pressure sensor, a density sensor, a viscosity sensor, a composition sensor, or any combination thereof. The optical assembly 500 can include one or more sensors 508 within or on the gas cell 502, along a portion of the bypass fluid line 212 (not shown), at other locations, or combinations thereof.

Figure 6:
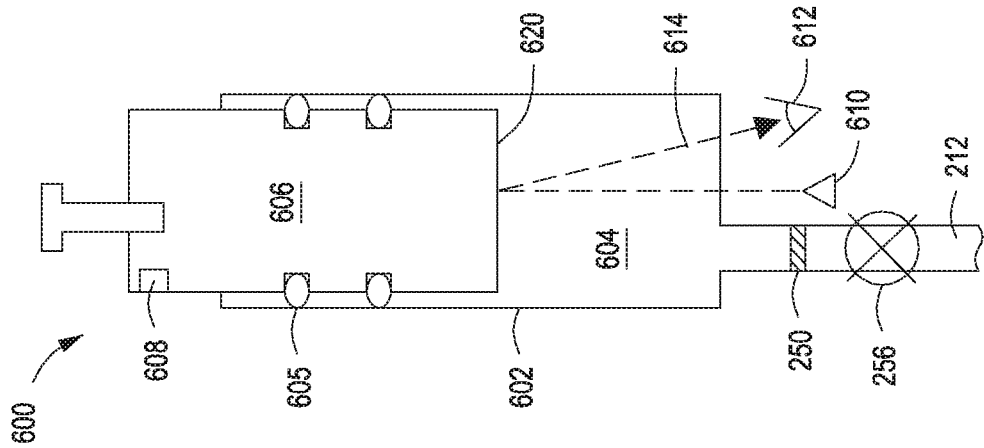
FIG. 6 depicts a schematic view of another optical assembly that is optionally used in a downhole tool for isolating and analyzing a gas, according to one or more embodiments.

The optical assembly 600 depicted in FIG. 6 includes a cell body 602, a moveable assembly 606 having one or more light sources 610, one or more optical detectors 612, and one or more reflective surfaces 620. For example, as depicted in FIG. 6, the optical assembly 600 has one light source 610, one optical detector 612, and one reflective surface 620. In other configurations, the optical assembly 600 includes 1, 2, 3, 4, 5, 6, or more for each of the light sources 610, the optical detectors 612, and the reflective surfaces 620.

The moveable assembly 606 can be or include, but is not limited to, a piston or a plunger. One or more sealing elements or sealants 605 are located between the cell body 602 and the moveable assembly 606 to produce a seal (e.g., gas and/or liquid seal) therebetween. The sealing element or sealant 605 can be or include, but is not limited to, one or more O-rings, one or more gaskets, grease, or any combination thereof. The cell body 602, the sealing element or sealant 605, and the moveable assembly 606 form a gas cell or chamber therebetween.

The reflective surface 620 is located on a lower surface of the moveable assembly 606 within the cell body 602. The reflective surface 620 can be or include one or more mirrors, one or more reflective coatings, and/or one or more arrays of mirrors.

The light source 610 and the optical detector 612 are located outside of the cell body 602 and the reflective surface 620 is inside the cell body 602, as depicted in FIG. 6. In other configurations, the light source 610 and the optical detector 612 can independently be inside or outside of the cell body 602. The optical detector 612 can be positioned on the same side of the cell body 602 relative to the light source 610, as depicted in FIG. 6. In other examples, not shown, the optical detector 612 can be positioned on an adjacent side and/or the opposite side of the cell body 602 relative to the light source 610.

The optical assembly 600 has an observation volume 604 defined by the available volume or space, fixed or variable, within the cell body 602. The optical assembly 600 receives the gas component from the gas separation assembly 240 and measure a property of the gas component within the observation volume 604 of the cell body 602 via the light source 610 and the optical detector 612.

The moveable assembly 606 is adjustable or otherwise moveable relative to the cell body 602. The moveable assembly 606 is axially moveable relative to the cell body 602 so to move away from the light source 610 to increase the volume of the observation volume 604 and toward the light source 610 to decrease the volume of the observation volume 604. The moveable assembly 606 can be moved by, but not limited to, a hydraulic motor, a pneumatic motor, an electric motor, or any combination thereof.

Optical beams emitted by the light source 610 follow the one or more light paths 614 that extend between any of the light sources 610, the reflective surfaces 620, and the optical detectors 612. For example, the light path 614 extends from the light source 610 to the reflective surface 620 and from the reflective surface 620 to the optical detector 612. An array of reflective surfaces 620 at different distances from the light source 610 can provide light paths 614 having proportionally different lengths. The moveable assembly 606 is axially moveable relative to the cell body 602 so to move away from the light source 610 to increase the length of the light path 614 and toward the light source 610 to decrease the length of the light path 614.

The optical assembly 600 can also include one or more sensors 608. The sensor 608 can be or include, but is not limited to, a temperature sensor, a pressure sensor, a combined temperature-pressure sensor, a density sensor, a viscosity sensor, a composition sensor, or any combination thereof. The optical assembly 600 can include one or more sensors 608 within or on the cell body 602 (not shown) or the moveable assembly 606, along a portion of the bypass fluid line 212 (not shown), at other locations, or combinations thereof.

Figure 7:
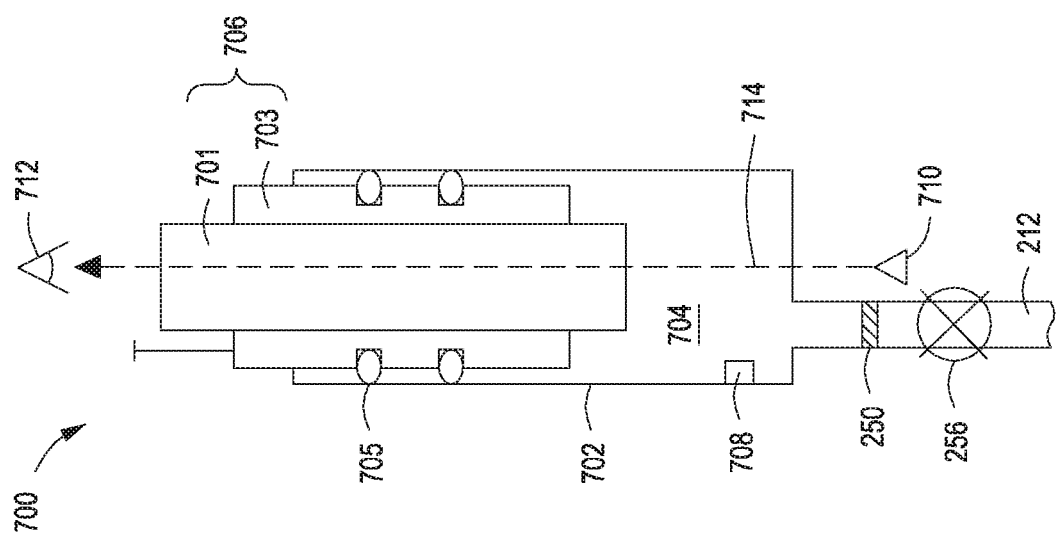
FIG. 7 depicts a schematic view of another optical assembly that is optionally used in a downhole tool for isolating and analyzing a gas, according to one or more embodiments.

The optical assembly 700 depicted in FIG. 7 includes a cell body 702, a moveable assembly 706, one or more light sources 710, and one or more optical detectors 712. For example, as depicted in FIG. 7, the optical assembly 700 has one light source 710 and one optical detector 712. In other configurations, the optical assembly 700 includes 1, 2, 3, 4, 5, 6, or more for each of the light sources 710 and the optical detectors 712.

The moveable assembly 706 includes one or more transparent segments 701 and one or more holders 703. The holder 703 is positioned between the transparent segment 701 and the cell body 702. The holder 703 is coupled to the transparent segment 701 and supports the transparent segment 701 in moveable positions relative to the cell body 702.

The transparent segment 701 can be or include one or more transparent materials. The holder 703 can be or include one or more transparent oxide and/or one or more transparent semiconductors. Exemplary transparent materials can be or include, but is not limited to, sapphire, aluminum oxide, quartz, glass, silicon oxide, silica (e.g., UV fused-silica), calcium fluoride, magnesium fluoride, or any combination thereof. The holder 703 can be or include one or more metals, ceramics, polymeric materials, or any combination thereof. In one or more examples, the moveable assembly 706 is or includes a transparent piston or plunger.

One or more sealing elements or sealants 705 are located between the cell body 702 and the moveable assembly 706 (e.g., the holder 703) to produce a seal (e.g., gas and/or liquid seal) therebetween. The sealing element or sealant 705 can be or include, but is not limited to, one or more O-rings, one or more gaskets, grease, or any combination thereof. The cell body 702, the sealing element or sealant 705, and the moveable assembly 706 form a gas cell or chamber therebetween.

The light source 710 and the optical detector 712 are located outside of the combined cell body 702 and the moveable assembly 706 (e.g., gas cell), as depicted in FIG. 7. In other configurations, the light source 710 and the optical detector 712 can independently be located inside or outside of the cell body 702. The optical detector 712 can be located on the opposite side of the cell body 702 relative to the light source 710, as depicted in FIG. 7.

The optical assembly 700 has an observation volume 704 defined by the available volume or space, fixed or variable, within the cell body 702. The optical assembly 700 receives the gas component from the gas separation assembly 240 and measure a property of the gas component within the observation volume 704 of the cell body 702 via the light source 710 and the optical detector 712.

The moveable assembly 706 is adjustable or otherwise moveable relative to the cell body 702. The moveable assembly 706 is axially moveable relative to the cell body 702 so to move away from the light source 710 to increase the volume of the observation volume 704 and toward the light source 710 to decrease the volume of the observation volume 704. The moveable assembly 706 can be moved by, but not limited to, a hydraulic motor, a pneumatic motor, an electric motor, or any combination thereof.

Optical beams emitted by the light source 710 follow the one or more light paths 714 that extend between any of the light sources 710 and the optical detectors 712. For example, the light path 714 extends from the light source 710, through the transparent segment 701, and to the optical detector 712. In one or more configurations, the optical detector 712 is attached or otherwise coupled to the moveable assembly 706 so that the optical detector 712 can be adjusted to different distances from the light source 710 to provide the light path 714 with variable or adjustable lengths. The moveable assembly 706 is axially moveable relative to the cell body 702 so to move away from the light source 710 to increase the length of the light path 714 and toward the light source 710 to decrease the length of the light path 714.

The optical assembly 700 can also include one or more sensors 708. The sensor 708 can be or include, but is not limited to, a temperature sensor, a pressure sensor, a combined temperature-pressure sensor, a density sensor, a viscosity sensor, a composition sensor, or any combination thereof. The optical assembly 700 can include one or more sensors 708 within or on the cell body 702, the moveable assembly 706 (not shown), along a portion of the bypass fluid line 212 (not shown), at other locations, or combinations thereof.

Figure 8:
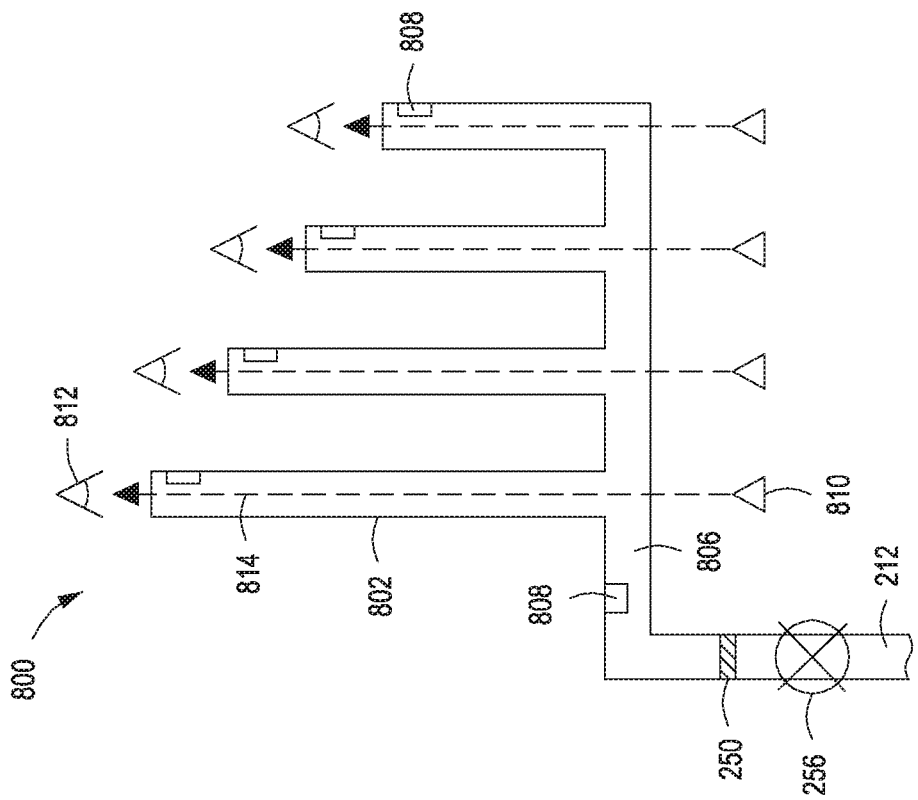
FIG. 8 depicts a schematic view of another optical assembly that is optionally used in a downhole tool for isolating and analyzing a gas, according to one or more embodiments.

The optical assembly 800 depicted in FIG. 8 includes one or more gas cells 802, one or more light sources 810, and one or more optical detectors 812. For example, as depicted in FIG. 8, the optical assembly 800 has four gas cells 802, four light sources 810, and four optical detectors 812. In other configurations, the optical assembly 800 includes 1, 2, 3, 4, 5, 6, or more for each of the gas cells 802, the light sources 810, and the optical detectors 812. A fluid line 806 is coupled to and between and in fluid communication with the bypass fluid line 212 and the gas cells 802.

The light source 810 and the optical detector 812 are located outside of the gas cells 802, as depicted in FIG. 8. In other configurations, not shown, any of the light sources 810 and/or the optical detectors 812 can independently be positioned inside or outside of the gas cells 802. The optical detector 812 can be located on the opposite side of the gas cell 802 relative to the light source 810, as depicted in FIG. 8. In other examples, not shown, the optical detector 812 can be positioned on the same side and/or an adjacent side of the gas cell 802 relative to the light source 810, if one or more reflective surfaces and/or mirrors (not shown) are located therebetween. Optical beams emitted by the light source 810 follow the light path 814 extending between each set of light source 810 and optical detector 812.

The optical assembly 800 has an observation volume 804 defined by the available volume or space, fixed or variable, within the gas cell 802. The optical assembly 800 receives the gas component from the gas separation assembly 240 and measure a property of the gas component within the observation volume 804 of the gas cell 802 via the light source 810 and the optical detector 812.

The optical assembly 800 can also include one or more sensors 808. The sensor 808 can be or include, but is not limited to, a temperature sensor, a pressure sensor, a combined temperature-pressure sensor, a density sensor, a viscosity sensor, a composition sensor, or any combination thereof. The optical assembly 800 can include one or more sensors 808 within or on the gas cell 802, along a portion of the fluid line 806, along a portion of the bypass fluid line 212 (not shown), at other locations, or combinations thereof.

Figure 9:
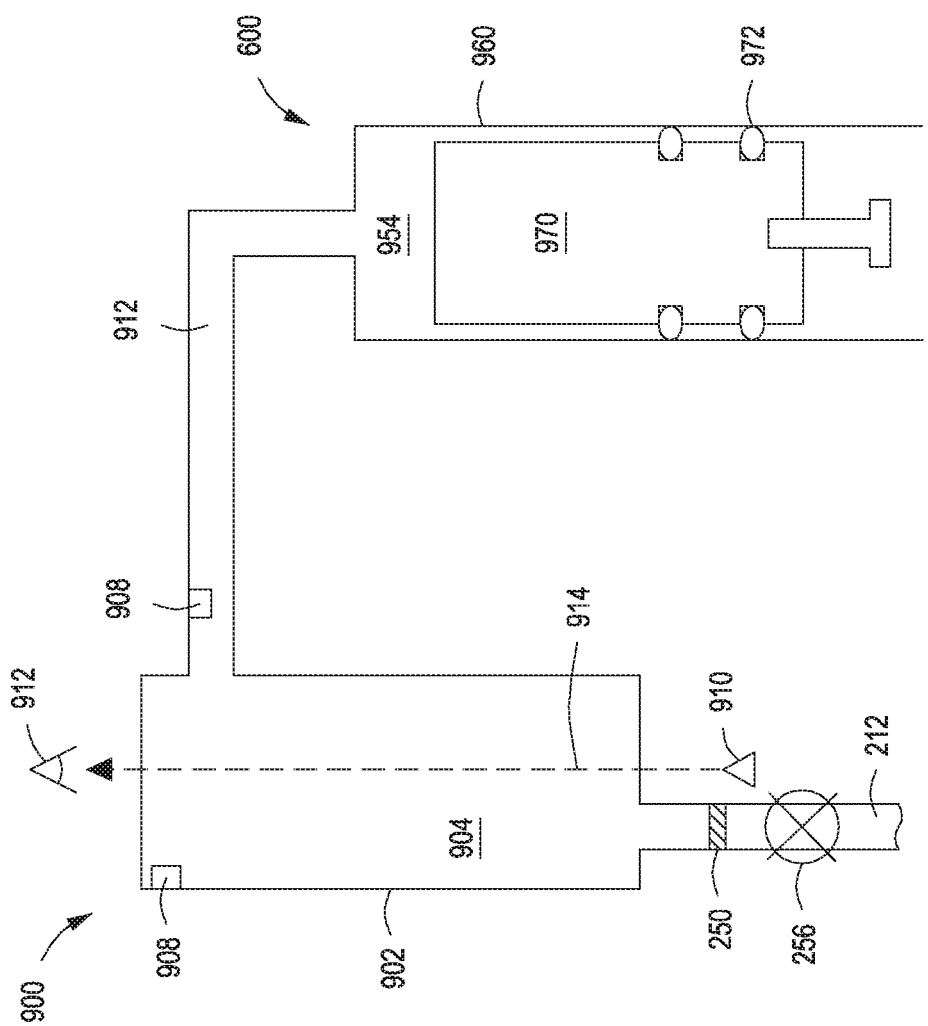
FIG. 9 depicts a schematic view of a gas mixing assembly and another optical assembly that are optionally used in a downhole tool for isolating and analyzing a gas, according to one or more embodiment.

FIG. 9 depicts a schematic view of an optical assembly 900 and a gas mixing assembly 950 that can be located in the gas analysis section 160 and used in the downhole tool 100, 200 to analyze one or more gas components, according to one or more embodiments. The optical assembly 900 includes one or more gas cells 902, one or more light sources 910, and one or more optical detectors 912. In other configurations, the optical assembly 900 includes 2, 3, 4, 5, 6, or more for each of the gas cells 902, the light sources 910, and the optical detectors 912.

The light source 910 and the optical detector 912 are located outside of the gas cells 902, as depicted in FIG. 9. In other configurations, not shown, the light source 910 and/or the optical detector 912 can independently be inside or outside of the gas cells 902. The optical detector 912 can be the opposite side of the gas cell 902 relative to the light source 910, as depicted in FIG. 9. In other examples, not shown, the optical detector 912 can be located on the same side and/or an adjacent side of the gas cell 902 relative to the light source 910, if one or more reflective surfaces and/or mirrors (not shown) are positioned therebetween. Optical beams emitted by the light source 910 follow the light path 914 extending between each set of light source 910 and optical detector 912.

The optical assembly 900 has an observation volume 904 defined by the available volume or space, fixed or variable, within the gas cell 902. The optical assembly 900 receives the gas component from the gas separation assembly 240 and measure a property of the gas component within the observation volume 904 of the gas cell 902 via the light source 910 and the optical detector 912.

The optical assembly 900 can also include one or more sensors 908. The sensor 908 can be or include, but is not limited to, a temperature sensor, a pressure sensor, a combined temperature-pressure sensor, a density sensor, a viscosity sensor, a composition sensor, or any combination thereof. The optical assembly 900 can include one or more sensors 908 within or on the gas cell 902, along a portion of a fluid line 912, along a portion of the bypass fluid line 212 (not shown), at other locations, or combinations thereof.

In one or more embodiments, the gas mixing assembly 950 is coupled to and in fluid communication with the optical assembly 900 by one or more fluid lines 912. In other embodiments, the gas mixing assembly 950 is coupled to and used with any of the optical assemblies 260, 500, 600, 700, or 800 depicted in FIGS. 2 and 5-8. As such, the optical assembly 900 can be substituted with any one or more optical assemblies 260, 500, 600, 700, or 800 depicted in FIGS. 2 and 5-8, or other optical assemblies that can be coupled to and in fluid communication with the bypass fluid line 212 and/or contained within the gas analysis section 160.

The gas mixing assembly 950 includes a moveable assembly 970 at least partially contained within a mixing body 960. The moveable assembly 970 is adjustable or otherwise moveable relative to the mixing body 960. The moveable assembly 970 can be or include, but is not limited to, a mixing piston or plunger. One or more sealing elements or sealants 972 are located between the mixing body 960 and the moveable assembly 970 to produce a seal (e.g., gas and/or liquid seal) therebetween. The sealing element or sealant 972 can be or include, but is not limited to, one or more O-rings, one or more gaskets, grease, or any combination thereof. The mixing body 960, the sealing element or sealant 972, and the moveable assembly 970 form a gas cell or chamber therebetween.

The gas mixing assembly 950 has a mixing volume 954 defined by the available volume or space, fixed or variable, within the mixing body 960. The gas mixing assembly 950 receives and combines the gas components from the observation volume 904 and the bypass fluid line 212. The gas components are combined or otherwise mixed within a combination of the observation volume 904, the fluid line 912, and the mixing volume 954.

The moveable assembly 970 is axially moveable relative to the mixing body 960 so to move away from the fluid line 912 to increase the volume of the mixing volume 954 and toward the fluid line 912 to decrease the volume of the mixing volume 954. The moveable assembly 970 can be moved by, but not limited to, a hydraulic motor, a pneumatic motor, an electric motor, or any combination thereof.

The gas mixing assembly 950 combines and/or mixes together the gaseous components located in the optical assembly 900 and the bypass fluid line 212. Mixing the gas components together provides removal of the gas component from the optical assembly 900 and a more uniform sample of the gas component than otherwise is available. The gas mixing assembly 950 combines and/or mixes together a first sample of the gaseous component in the optical assembly 900 and a second sample of the gas component in the bypass fluid line 212. A pressure oscillation from the bypass fluid line 212 combines and/or mixes together the first sample of the gaseous component in the optical assembly 900 and the second sample of the gas component in the bypass fluid line 212.

FIG. 10 depicts a schematic view of a liquid rejection device 1000 that is optionally used in the downhole tool 100, 200, according to one or more embodiments. The liquid rejection device 1000 is coupled to and used as the liquid rejection device 250 on any of the optical assemblies 260, 500, 600, 700, 800, or 900 depicted in FIGS. 2 and 5-9, or other optical assemblies that are coupled to and in fluid communication with the bypass fluid line 212 and/or contained within the gas analysis section 160.

The liquid rejection device 1000 includes one or more liquid traps 1010, one or more purge assemblies 1020, and one or more valves 1016 coupled to and in fluid communication with one or more fluid lines 1002. The fluid line 1002 is coupled to the bypass fluid line 212 at junction 1050 and coupled to the primary fluid line 210 at junction 1052, as depicted in FIG. 10. A first portion of the fluid line 1002 located between the junction 1050 and the liquid trap 1010 can be or include a trap line. Similarly, a second portion of the fluid line 1002 located between the liquid trap 1010 and the junction 1052 can be or include a purge line. As such, the trap line is coupled to and between the liquid trap 1010 and the bypass fluid line 212, and the purge line is coupled to and between the liquid trap 1010 and the primary fluid line 210.

The liquid trap 1010 reduces or prevents the liquid component from entering into the optical assemblies 260, 500, 600, 700, 800, or 900 via the bypass fluid line 212. In some examples, the liquid trap 1010 cools and/or condenses gas and/or stores liquid therein. The purge assembly 1020 is used to transfer the liquid component from the liquid trap 1010, through the fluid line 1002, and to the primary fluid line 210.

The purge assembly 1020 includes a moveable assembly 1024 at least partially located within a purging body 1022. The moveable assembly 1024 is adjustable or otherwise moveable relative to the purging body 1022. The moveable assembly 1024 can be or include, but is not limited to, a piston or a plunger. One or more sealing elements or sealants 1026 are located between the purging body 1022 and the moveable assembly 1024 to produce or form a seal (e.g., gas and/or liquid seal) therebetween. The sealing element or sealant 1026 can be or include, but is not limited to, one or more O-rings, one or more gaskets, grease, or any combination thereof. The purging body 1022, the sealing element or sealant 1026, and the moveable assembly 1024 form a gas cell or chamber therebetween.

The purge assembly 1020 has a purge volume 1028 defined by the available volume or space, fixed or variable, within the purging body 1022. The purge assembly 1020 purges the gas components from the liquid trap 1010 and/or the fluid line 1002 and into the primary fluid line 210.

The moveable assembly 1024 is axially moveable relative to the purging body 1022 so to move away from the fluid line 1002 to increase the volume of the purge volume 1028 and toward the fluid line 1002 to decrease the volume of the purge volume 1028. The moveable assembly 1024 can be moved by, but not limited to, a hydraulic motor, a pneumatic motor, an electric motor, or any combination thereof.

Figure 11:
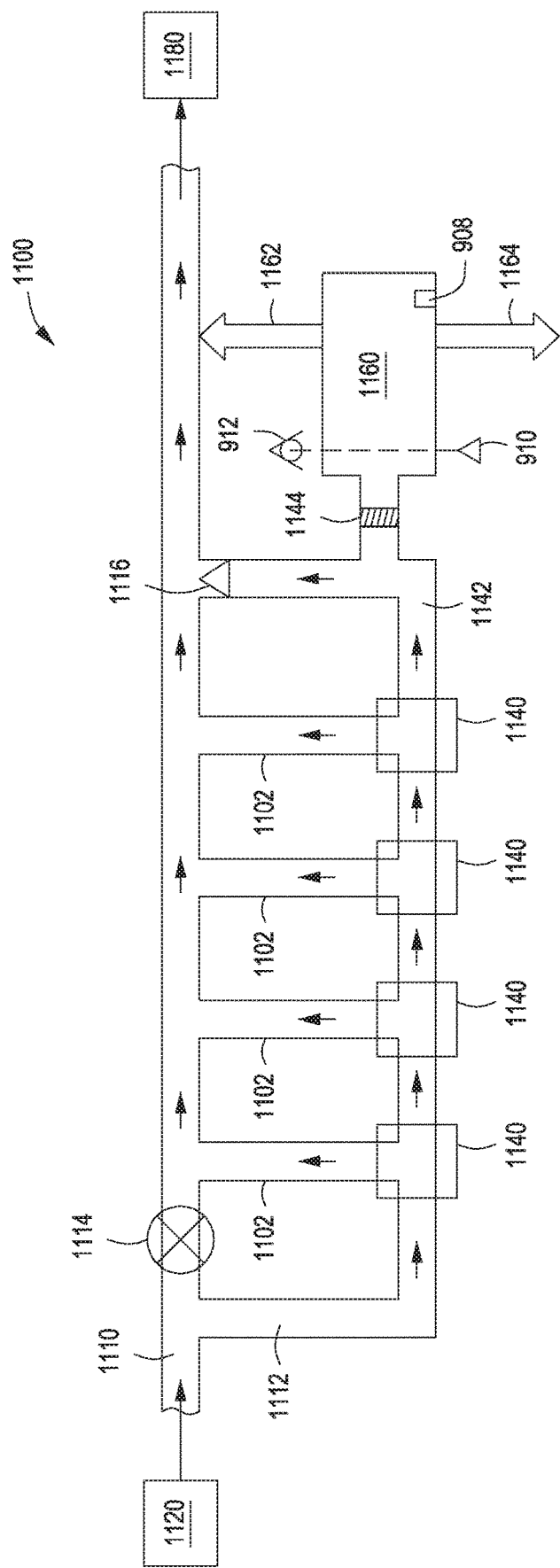
FIG. 11 depicts a schematic view of another downhole tool for isolating and analyzing a gas, according to one or more embodiments.

FIG. 11 depicts a schematic view of a downhole tool 1100 for isolating and analyzing a gas, according to one or more embodiments. One or more bypass fluid lines 1112 are coupled to and in fluid communication with the primary fluid line 1110, such as at one, two, or more junctions along the primary fluid line 1110 between the fluid acquisition assembly 1120 and the pump assembly 1180. The primary fluid line 1110 and the bypass fluid line 1112 are isolatable from one another by one, two, or more valves 1114, 1116 used to control the fluid communication therebetween. Each of the valves 1114, 1116 is independently a stop valve, a two-way valve, a three-way valve, or a check valve (e.g., one-way check valve). In some examples, the valve 1114 includes a stop valve or a two-way valve and the valve 1116 includes a one-way check valve.

The downhole formation fluid is diverted from the primary fluid line 1110 to the bypass fluid line 1112 via the valve 1114. The downhole formation fluid flows or passes through one or more liquid-gas separators 1140 (four liquid-gas separators 1140 are depicted in FIG. 11) that are coupled the bypass fluid line 1112. The liquid-gas separators 1140 are at least partially separate or completely separate one or more gas components and one or more liquid components from the downhole formation fluid. The gas components or a gas-rich component flows or passes from the liquid-gas separator 1140 via the bypass fluid line 1112 and the liquid components or the liquid-rich components flows or passes from the liquid-gas separator 1140 via the fluid line 1102 to the primary fluid line 1110. Two, three, four, or more of the liquid-gas separators 1140 are serially coupled along the bypass fluid line 1112 to further remove liquid from the gas components or the gas-rich component to produce one or more purified gas components in fluid line 1142.

The purified gas component in fluid line 1142 flows or passes through one or more liquid rejection devices 1144. The liquid rejection device 1144 reduces and/or prevents water or other liquids from flowing into an optical assembly 1160. The liquid rejection device 1144 can be or include, but is not limited to, one or more gas permeable membranes, a liquid or solvent trap, a centrifuge, or any combination thereof. In some examples, the liquid rejection device 1144 can be the same device as the liquid rejection device 250 or 1000.

The optical assembly 1160 includes one or more sensors 908, one or more light sources 910, and/or one or more optical detectors 912, as described and discussed above. One or more transfer lines 1162 is or includes a fluid line and a control valve coupled to and between the optical assembly 1160 and the primary fluid line 1110. Each sample of the gas component is transferred or otherwise flowed from the optical assembly 1160 to the primary fluid line 1110 via the transfer line 1162 subsequent the data collection. Alternatively, one or more purge lines 1164 can be or include a fluid line and a control valve coupled to and extending into the wellbore, such as away from the optical assembly 1160 and away from the downhole tool 1100, as depicted in FIG. 11.

In one or more embodiments, a method for isolating and analyzing a gas with one or more downhole tools (including, but not limited to, the downhole tools 100, 200, 1100, and/or other types of downhole tools) can include flowing a downhole formation fluid from a subterranean formation into a fluid line within the downhole tool, flowing the downhole formation fluid into a gas separation assembly coupled to the fluid line, separating a gas component and a liquid component from the downhole formation fluid within the gas separation assembly, flowing the gas component from the gas separation assembly to an optical assembly coupled to the fluid line, and measuring a property of the gas component within the optical assembly via an optical detector.

In other embodiments, a method for isolating and analyzing a gas with one or more downhole tools (including, but not limited to, the downhole tools 100, 200, 1100, and/or other types of downhole tools) can include flowing a downhole formation fluid from a subterranean formation into a primary fluid line within the downhole tool, diverting the downhole formation fluid from the primary fluid line to a bypass fluid line within the downhole tool, flowing the downhole formation fluid into a gas separation assembly coupled to the bypass fluid line, separating a gas component and a liquid component from the downhole formation fluid within the gas separation assembly, flowing the gas component from the gas separation assembly to an optical assembly coupled to the bypass fluid line, measuring a property of the gas component within the optical assembly via an optical detector, and diverting the downhole formation fluid from the bypass fluid line to the primary fluid line.

The gas component can be removed from the optical assembly and the liquid component can be removed from the gas separation assembly. The property of the gas component can be measured by passing light from a light source, through the gas component in the optical assembly, and to the optical detector. The gas separation assembly can include a piston located at least partially within a body or housing and a separation volume defined between the piston and the body or housing. The gas component and the liquid component are separated from the downhole formation fluid within the separation volume.

In other embodiments, a method for isolating and analyzing a gas with one or more downhole tools (including, but not limited to, the downhole tools 100, 200, 1100, and/or other types of downhole tools) can include determining one or more components of a gas phase with an isolatable gas measurement cell located in hydraulic communication with and above a bypass fluid line in which one or more gas components can be separated from one or more liquid components derived from a downhole fluid.

The flow can be diverted through the bypass fluid line when a predominately suitable for measurement gas phase is detected. The suitability can be determined by sensors on the primary fluid line. The sensors can be located in the divertible or isolatable fluid line section.

The isolatable gas component measurement sensor can remain isolated until the gas component is suitable for measurement. One or more sensors on the bypass fluid line can be used to determine suitability for measurement. The sensors on the bypass fluid line can be or include at least one density sensor. The sensors located on the bypass fluid line can be or include one or more heat capacity sensors located along the bypass fluid line.

The method can include flowing an enhanced split stream gas through the gas measurement section with return to the primary fluid line, and also include flowing liquid through the main bypass return line to the primary fluid line. The method can include choking at least one of the return fluid lines to optimize the split flow. The method can also include enhancing the separation of the gas and liquid components with a liquid separation mechanism. The liquid separation can be achieved by one of density or viscosity differences between a gas phase and a liquid phase.

One or more fluid parameters (chemical and or physical) of at least one of the gas or liquid phases can be measured. The parameters can be measured at multiple temperatures and or pressures. An equation of state can be derived by measured parameters. The equation of state can be used to determine the optimal conditions under which to make a gas component measurement.

The gas component measurement can be extrapolated to reservoir levels for the reservoir fluid. The extrapolation can be achieved by an asymptotic fit to either pump volume or pump time. The extrapolated gas component level can be used to determine sampling parameters. In some examples, the sampling parameter can be sampling time (including never). In other examples, the sampling parameter can be wellbore sampling position to sample. The reservoir extrapolation can be used to optimize a DST plan.

The fluid (the liquid component, the gas component, or a mixture thereof) can be purged after the measurement, such as being purged to the wellbore and/or to the primary fluid line. The fluid can be flushed through the bypass fluid line before a measurement to minimize carry over from a previous measurement. The gas of the optical section can be flushed to minimize carryover prior to a measurement. One or more previous measurements can be utilized to calculate a carryover effect. The carryover measurement can be used to correct the present measurement value.

One or more sensor measurements can be used to determine how to make an optimal measurement. The sensor measurements can be generated from one or more pressure sensors, one or more composition sensors, one or more temperature sensors, one or more density sensors, or any combination thereof. One or more sensors can be located or otherwise positioned on a bypass fluid line and one or more sensors can be located or otherwise positioned in an optical section, such as any of the optical assemblies. The method can include operating the separation of the gas and liquid components as a continuous flow process.

Measurements of the gas components can be made by optical equipment that can include, but is not limited to, one or more light sources, one or more optical detector, or combination thereof. The optimal path length can be selected by pressure. The pressure can be used to tune the optical measurements.

In addition to the embodiments described above, embodiments of the present disclosure further relate to one or more of the following paragraphs:

1. A downhole tool for isolating and analyzing a gas, comprising: a gas separation assembly comprising a piston disposed at least partially within a housing and a separation volume defined between the piston and the housing, wherein the piston is movable to separate a gas component and a liquid component from a downhole formation fluid within the separation volume; and a gas specific analyzer in fluid communication with the gas separation assembly and operable to measure a property of the gas component.

2. A downhole tool for isolating and analyzing a gas, comprising: a fluid acquisition assembly operable to receive a downhole formation fluid; a primary fluid line coupled to and in fluid communication with the fluid acquisition assembly; a bypass fluid line coupled to and in fluid communication with the primary fluid line; a gas separation assembly in fluid communication with the bypass fluid line and comprising a piston disposed at least partially within a housing and a separation volume defined between the piston and the housing, the piston being moveable to separate a gas component and a liquid component from the downhole formation fluid within the separation volume; and a gas specific analyzer in fluid communication with the gas separation assembly and operable to measure a property of the gas component.

3. The downhole tool according to paragraph 1 or 2, wherein the gas specific analyzer is an optical assembly comprising a light source, an optical detector, and a gas cell containing an observation volume, and wherein the optical assembly is operable to measure a property of the gas component within the observation volume via the light source and the optical detector.

4. A downhole tool for isolating and analyzing a gas, comprising: a fluid acquisition assembly configured to receive a downhole formation fluid; a primary fluid line coupled to and in fluid communication with the fluid acquisition assembly; a bypass fluid line coupled to and in fluid communication with the primary fluid line; a gas separation assembly coupled to and in fluid communication with the bypass fluid line, wherein the gas separation assembly comprises a piston disposed at least partially within a body and a separation volume defined between the piston and the body, and wherein the gas separation assembly is configured to receive the downhole formation fluid from the bypass fluid line and separate a gas component and a liquid component from the downhole formation fluid within the separation volume; and an optical assembly coupled to and in fluid communication with the bypass fluid line, wherein the optical assembly comprises a light source, an optical detector, and a gas cell having an observation volume, and wherein the optical assembly is configured to receive the gas component from the gas separation assembly and measure a property of the gas component within the observation volume via the light source and the optical detector.

5. A downhole tool for isolating and analyzing a gas, comprising: a fluid acquisition assembly configured to receive a downhole formation fluid; a primary fluid line coupled to and in fluid communication with the fluid acquisition assembly; a bypass fluid line coupled to and in fluid communication with the primary fluid line; a gas separation assembly coupled to and in fluid communication with the bypass fluid line, wherein: the gas separation assembly comprises a piston disposed at least partially within a body and a separation volume defined between the piston and the body, the gas separation assembly is configured to receive the downhole formation fluid from the bypass fluid line and separate a gas component and a liquid component from the downhole formation fluid within the separation volume, the gas separation assembly further comprises a fluid port disposed in an upper portion of the body, and the fluid port is configured to introduce the downhole formation fluid into the separation volume above an upper surface of the piston; and an optical assembly coupled to and in fluid communication with the bypass fluid line, wherein: the optical assembly comprises a light source, an optical detector, and a gas cell having an observation volume, and the optical assembly is configured to receive the gas component from the gas separation assembly and measure a property of the gas component within the observation volume via the light source and the optical detector.

6. A method for isolating and analyzing a gas with a downhole tool, comprising: flowing a downhole formation fluid from a subterranean formation into a fluid line within the downhole tool; flowing the downhole formation fluid into a gas separation assembly coupled to the fluid line; separating a gas component and a liquid component from the downhole formation fluid within the gas separation assembly; flowing the gas component from the gas separation assembly to an optical assembly coupled to the fluid line; and measuring a property of the gas component within the optical assembly via an optical detector.

7. A method for isolating and analyzing a gas with a downhole tool, comprising: flowing a downhole formation fluid from a subterranean formation into a fluid line within the downhole tool; flowing the downhole formation fluid into a gas separation assembly coupled to the fluid line; separating a gas component and a liquid component from the downhole formation fluid within the gas separation assembly; flowing the gas component from the gas separation assembly to a gas specific analyzer coupled to the fluid line; and measuring a property of the gas component with the gas specific analyzer.

8. The method of paragraph 7, further comprising: removing the gas component from the gas specific analyzer; and removing the liquid component from the gas separation assembly.

9. The method of paragraph 7, wherein the gas specific analyzer is an optical assembly and the property of the gas component is measured within the optical assembly via an optical detector.

10. The method of paragraph 9, wherein measuring the property of the gas component further comprises passing light from a light source through the gas component in the optical assembly and to the optical detector, wherein the gas separation assembly comprises a piston disposed at least partially within a housing and a separation volume defined between the piston and the housing, and wherein the gas component and the liquid component are separated from the downhole formation fluid within the separation volume.

11. A method for isolating and analyzing a gas with a downhole tool, comprising: flowing a downhole formation fluid from a subterranean formation into a primary fluid line within the downhole tool; diverting the downhole formation fluid from the primary fluid line to a bypass fluid line within the downhole tool; flowing the downhole formation fluid into a gas separation assembly coupled to the bypass fluid line; separating a gas component and a liquid component from the downhole formation fluid within the gas separation assembly; flowing the gas component from the gas separation assembly to a gas specific analyzer coupled to the bypass fluid line; measuring a property of the gas component with the gas specific analyzer; and diverting the downhole formation fluid from the bypass fluid line to the primary fluid line.

12. The method according to any one of paragraphs 6-11, wherein the gas specific analyzer is an optical assembly and the property of the gas component is measured within the optical assembly via an optical detector.

13. The downhole tool or the method according to any one of paragraphs 1-12, wherein the gas specific analyzer is an optical assembly comprising a light source, an optical detector, and a gas cell containing an observation volume, wherein the optical assembly is operable to measure a property of the gas component within the observation volume via the light source and the optical detector.

14. The downhole tool or the method according to paragraph 13, further comprising: a fluid acquisition assembly operable to receive a downhole formation fluid; a primary fluid line coupled to and in fluid communication with the fluid acquisition assembly; and a bypass fluid line coupled to and in fluid communication with the primary fluid line; wherein the gas separation assembly is coupled to and in fluid communication with the bypass fluid line and receives the downhole formation fluid from the bypass fluid line; and wherein the optical assembly is coupled to and in fluid communication with the bypass fluid line and receives the gas component from the gas separation assembly.

15. The downhole tool or the method according to paragraph 14, wherein a first fluid sensor is disposed on the bypass fluid line upstream of the gas separation assembly and configured to measure the density of the downhole formation fluid before entering the gas separation assembly, and wherein a second fluid sensor is disposed on the bypass fluid line downstream of the gas separation assembly and configured to measure the density of the downhole formation fluid after exiting the gas separation assembly.

16. The downhole tool or the method according to paragraph 14, wherein the primary fluid line and the bypass fluid line are isolatable from one another by two or more valves configured to control the fluid communication therebetween.

17. The downhole tool or the method according to paragraph 14, wherein a liquid rejection device is disposed on the bypass fluid line between the gas separation assembly and the optical assembly.

18. The downhole tool or the method according to paragraph 17, wherein the liquid rejection device comprises a gas permeable membrane, a liquid trap, a centrifuge, or any combination thereof.

19. The downhole tool or the method according to paragraph 17, wherein the liquid rejection device comprises a liquid trap, a trap line, a purge assembly, and a purge line, wherein the trap line is coupled to and between the liquid trap and the bypass fluid line, and wherein the purge line is coupled to and between the liquid trap and the primary fluid line.

20. The downhole tool or the method according to paragraph 14, wherein the bypass fluid line further comprises an exit line having an exit port extending outside of the downhole tool and isolatable by a valve.

21. The downhole tool or the method according to paragraph 14, further comprising a temperature sensor, a pressure sensor, a combined temperature-pressure sensor, a density sensor, a viscosity sensor, a composition sensor, or any combination thereof disposed within the optical assembly, the bypass fluid line, or both of the optical assembly and the bypass fluid line.

22. The downhole tool or the method according to paragraph 14, further comprising a fluid probe assembly coupled to the primary fluid line upstream of the bypass fluid line and comprising a probe extending away from the fluid acquisition assembly outside of the downhole tool.

23. The downhole tool or the method according to paragraph 22, further comprising a pre-test unit disposed in the fluid acquisition assembly and coupled to the primary fluid line downstream of the fluid probe assembly and upstream of the bypass fluid line.

24. The downhole tool or the method according to any one of paragraphs 1-23, wherein the gas separation assembly further comprises a fluid slit disposed along a vertical side of the inside of the housing, and wherein the fluid slit allows the downhole formation fluid to be introduced into the separation volume along the vertical side of the housing and above the piston.

25. The downhole tool or the method according to any one of paragraphs 1-24, wherein the gas separation assembly further comprises a first plurality of fluid slits disposed along a first vertical side of the inside of the housing and a second plurality of fluid slits disposed along a second vertical side of the inside of the housing, and wherein the fluid slits allow the downhole formation fluid to be introduced into the separation volume along the vertical sides of the housing and above the piston.

26. The downhole tool or the method according to paragraph 25, wherein the gas separation assembly further comprises a fluid passageway disposed at least partially around a circumference of the inside of the housing, and wherein the first and second pluralities of the fluid slits are in fluid communication with the fluid passageway.

27. The downhole tool or the method according to paragraph 13-26, wherein the optical assembly further comprises a reflective surface along a light path extending from the light source to the optical detector.

28. The downhole tool or the method according to paragraph 27, wherein the reflective surface is stationary or fixed relative to the light source and the optical detector, and wherein the reflective surface reflects light along a fixed length of the light path.

29. The downhole tool or the method according to paragraph 27, wherein the reflective surface is moveable relative to the light source and the optical detector, and wherein the reflective surface reflects light along an adjustable length of the light path.

30. The downhole tool or the method according to paragraph 13-29, wherein the optical assembly further comprises a transparent segment and a cell body at least partially defining the observation volume within the optical cell.

31. The downhole tool or the method according to paragraph 30, wherein the optical assembly further comprises a holder disposed between the transparent segment and the cell body, wherein the holder supports the transparent segment in a moveable position relative to the cell body, and wherein the transparent segment comprises sapphire, aluminum oxide, quartz, glass, silicon oxide, silica, calcium fluoride, magnesium fluoride, or any combination thereof.

32. The downhole tool or the method according to paragraph 13-31, wherein the light source emits in at least the ultraviolet spectrum and comprises a deuterium lamp, a mercury lamp, or a combination thereof, and wherein the optical detector comprises an integrated computational element core.

33. The downhole tool or the method according to any one of paragraphs 1-32, wherein the gas component comprises mercury, hydrogen sulfide, a mercaptan, or any mixture thereof, and wherein the liquid component comprises crude oil, downhole water, drilling fluid, drilling fluid filtrate, or any mixture thereof.

34. The downhole tool or the method according to any one of paragraphs 1-33, further comprising a gas mixing assembly coupled to and in fluid communication with the gas specific analyzer.

One or more specific embodiments of the present disclosure have been described. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time-consuming, but would nevertheless be a routine undertaking of design, fabrication, and manufacture for those of ordinary skill having the benefit of this disclosure.

In the following discussion and in the claims, the articles "a," "an," and "the" are intended to mean that there are one or more of the elements. The terms "including," "comprising," and "having" and variations thereof are used in an open-ended fashion, and thus should be interpreted to mean "including, but not limited to . . . " Also, any use of any form of the terms "connect," "engage," "couple," "attach," "mate," "mount," or any other term describing an interaction between elements is intended to mean either an indirect or a direct interaction between the elements described. In addition, as used herein, the terms "axial" and "axially" generally mean along or parallel to a central axis (e.g., central axis of a body or a port), while the terms "radial" and "radially" generally mean perpendicular to the central axis. The use of "top," "bottom," "above," "below," "upper," "lower," "up," "down," "vertical," "horizontal," and variations of these terms is made for convenience, but does not require any particular orientation of the components.

Certain terms are used throughout the description and claims to refer to particular features or components. As one skilled in the art will appreciate, different persons may refer to the same feature or component by different names. This document does not intend to distinguish between components or features that differ in name but not function.

Reference throughout this specification to "one embodiment," "an embodiment," "an embodiment," "embodiments," "some embodiments," "certain embodiments," or similar language means that a particular feature, structure, or characteristic described in connection with the embodiment may be included in at least one embodiment of the present disclosure. Thus, these phrases or similar language throughout this specification may, but do not necessarily, all refer to the same embodiment.

Certain embodiments and features have been described using a set of numerical upper limits and a set of numerical lower limits. It should be appreciated that ranges including the combination of any two values, e.g., the combination of any lower value with any upper value, the combination of any two lower values, and/or the combination of any two upper values are contemplated unless otherwise indicated. Certain lower limits, upper limits and ranges appear in one or more claims below. All numerical values are "about" or "approximately" the indicated value, and take into account experimental error and variations that would be expected by a person having ordinary skill in the art.

The embodiments disclosed should not be interpreted, or otherwise used, as limiting the scope of the disclosure, including the claims. It is to be fully recognized that the different teachings of the embodiments discussed may be employed separately or in any suitable combination to produce desired results. In addition, one skilled in the art will understand that the description has broad application, and the discussion of any embodiment is meant only to be exemplary of that embodiment, and not intended to suggest that the scope of the disclosure, including the claims, is limited to that embodiment.

What is claimed is:

1. A downhole tool for isolating and analyzing a gas, comprising:
   a gas separation assembly comprising a piston disposed at least partially within a housing and a separation volume defined between the piston and the housing, wherein the piston is movable to separate a gas component and a liquid component from a downhole formation fluid within the separation volume;
   a gas specific analyzer in fluid communication with the gas separation assembly and operable to measure a property of the gas component;
   a fluid acquisition assembly operable to receive a downhole formation fluid;
   a primary fluid line coupled to and in fluid communications with the fluid acquisition assembly;
   a bypass fluid line coupled to and in fluid communication with the primary fluid line; and
   a liquid rejection device disposed on the bypass fluid line between the gas separation assembly and the gas specific analyzer;
   wherein the gas separation assembly is coupled to and in fluid communication with the bypass fluid line and receives the downhole formation fluid from the bypass fluid line;
   wherein the gas specific analyzer is coupled to and in fluid communication with the bypass fluid line and receives the gas component from the gas separation assembly; and
   wherein the liquid rejection device is in fluid communication with the primary fluid line.

2. The downhole tool of claim 1, wherein the gas specific analyzer is an optical assembly comprising a light source, an optical detector, and a gas cell containing an observation volume, and wherein the optical assembly is operable to measure a property of the gas component within the observation volume via the light source and the optical detector.

3. The downhole tool of claim 2, wherein the optical assembly further comprises a reflective surface disposed along a light path extending from the light source to the optical detector, wherein the reflective surface is stationary or fixed relative to the light source and the optical detector, and wherein the reflective surface reflects light along a fixed length of the light path.

4. The downhole tool of claim 2, wherein the optical assembly further comprises a reflective surface disposed along a light path extending from the light source to the optical detector, wherein the reflective surface is moveable relative to the light source and the optical detector, and wherein the reflective surface reflects light along an adjustable length of the light path.

5. The downhole tool of claim 2, wherein the optical assembly further comprises a transparent segment and a cell body at least partially defining the observation volume within the optical cell, wherein the optical assembly further comprises a holder disposed between the transparent segment and the cell body, wherein the holder supports the transparent segment in a moveable position relative to the cell body, and wherein the transparent segment comprises sapphire, aluminum oxide, quartz, glass, silicon oxide, silica, calcium fluoride, magnesium fluoride, or any combination thereof.

6. The downhole tool of claim 2, wherein the light source emits in at least the ultraviolet spectrum and comprises a deuterium lamp, a mercury lamp, or a combination thereof, and wherein the optical detector comprises an integrated computational element core.

7. The downhole tool of claim 1, wherein a first fluid sensor is disposed on the bypass fluid line upstream of the gas separation assembly and configured to measure the density of the downhole formation fluid before entering the gas separation assembly, and wherein a second fluid sensor is disposed on the bypass fluid line downstream of the gas separation assembly and configured to measure the density of the downhole formation fluid after exiting the gas separation assembly.

8. The downhole tool of claim 1, wherein:
the primary fluid line and the bypass fluid line are isolatable from one another by two or more valves configured to control the fluid communication therebetween; or
the bypass fluid line further comprises an exit line having an exit port extending outside of the downhole tool and isolatable by a valve.

9. The downhole tool of claim 1, wherein
the liquid rejection device comprises a gas permeable membrane, a liquid trap, a centrifuge, or any combination thereof; or
the liquid rejection device comprises a liquid trap, a trap line, a purge assembly, and a purge line, wherein the trap line is coupled to and between the liquid trap and the bypass fluid line, and wherein the purge line is coupled to and between the liquid trap and the primary fluid line.

10. The downhole tool of claim 1, further comprising a temperature sensor, a pressure sensor, a combined temperature-pressure sensor, a density sensor, a viscosity sensor, a composition sensor, or any combination thereof disposed within the gas specific analyzer, the bypass fluid line, or both of the optical assembly and the bypass fluid line.

11. The downhole tool of claim 1, further comprising a fluid probe assembly coupled to the primary fluid line upstream of the bypass fluid line and comprising a probe extending away from the fluid acquisition assembly outside of the downhole tool.

12. The downhole tool of claim 11, further comprising a pre-test unit disposed in the fluid acquisition assembly and coupled to the primary fluid line downstream of the fluid probe assembly and upstream of the bypass fluid line.

13. The downhole tool of claim 1, wherein the gas component comprises mercury, hydrogen sulfide, a mercaptan, or any mixture thereof, and wherein the liquid component comprises crude oil, downhole water, drilling fluid, drilling fluid filtrate, or any mixture thereof.

14. The downhole tool of claim 1, further comprising a gas mixing assembly coupled to and in fluid communication with the gas specific analyzer.

15. A downhole tool for isolating and analyzing a gas, comprising:
a gas separation assembly comprising a piston disposed at least partially within a housing and a separation volume defined between the piston and the housing, wherein the piston is movable to separate a gas component and a liquid component from a downhole formation fluid within the separation volume; and
a gas specific analyzer in fluid communication with the gas separation assembly and operable to measure a property of the gas component,
wherein the gas separation assembly further comprises a fluid slit disposed along a vertical side of the inside of the housing, and wherein the fluid slit allows the downhole formation fluid to be introduced into the separation volume along the vertical side of the housing and above the piston.

16. A downhole tool for isolating and analyzing a gas, comprising:
a gas separation assembly comprising a piston disposed at least partially within a housing and a separation volume defined between the piston and the housing, wherein the piston is movable to separate a gas component and a liquid component from a downhole formation fluid within the separation volume; and
a gas specific analyzer in fluid communication with the gas separation assembly and operable to measure a property of the gas component,
wherein the gas separation assembly further comprises a first plurality of fluid slits disposed along a first vertical side of the inside of the housing and a second plurality of fluid slits disposed along a second vertical side of the inside of the housing, and wherein the fluid slits allow the downhole formation fluid to be introduced into the separation volume along the vertical sides of the housing and above the piston.

17. The downhole tool of claim 16, wherein the gas separation assembly further comprises a fluid passageway disposed at least partially around a circumference of the inside of the housing, and wherein the first and second pluralities of the fluid slits are in fluid communication with the fluid passageway.

18. A method for isolating and analyzing a gas with a downhole tool, comprising:
flowing a downhole formation fluid from a subterranean formation into a primary fluid line within the downhole tool;
diverting the downhole formation fluid from the primary fluid line to a bypass fluid line within the downhole tool;
flowing the downhole formation fluid into a gas separation assembly coupled to the bypass fluid line;
separating a gas component and a liquid component from the downhole formation fluid within the gas separation assembly;
flowing the gas component from the gas separation assembly to a gas specific analyzer coupled to the bypass fluid line;
measuring a property of the gas component with the gas specific analyzer; and
diverting the downhole formation fluid from the bypass fluid line to the primary fluid line.

* * * * *